(12) United States Patent
Lewinski et al.

(10) Patent No.: US 9,217,104 B2
(45) Date of Patent: Dec. 22, 2015

(54) LUMINESCENT COMPOUNDS, METHOD OF PREPARATION OF LUMINESCENT COMPOUNDS AND APPLICATIONS THEREOF

(75) Inventors: Janusz Zbigniew Lewinski, Jozefow (PL); Kamil Sokolowski, Warsaw (PL)

(73) Assignee: Instytut Chemii Fizycznej Polskiejakademii Nauk, Warsaw (PL)

( * ) Notice: Subject to any disclaimer, the term of this patent is extended or adjusted under 35 U.S.C. 154(b) by 0 days.

(21) Appl. No.: 13/808,907

(22) PCT Filed: Jul. 6, 2011

(86) PCT No.: PCT/PL2011/000070
§ 371 (c)(1),
(2), (4) Date: Jan. 30, 2013

(87) PCT Pub. No.: WO2012/005615
PCT Pub. Date: Jan. 12, 2012

(65) Prior Publication Data
US 2013/0131345 A1 May 23, 2013

(30) Foreign Application Priority Data
Jul. 7, 2010 (PL) ......................................... 391776

(51) Int. Cl.
| | |
|---|---|
| C07D 215/00 | (2006.01) |
| C09K 11/06 | (2006.01) |
| C07F 3/00 | (2006.01) |
| C07F 3/06 | (2006.01) |
| H01L 51/00 | (2006.01) |
| H05B 33/14 | (2006.01) |
| H05B 33/22 | (2006.01) |
| H01L 51/50 | (2006.01) |

(52) U.S. Cl.
CPC ................ C09K 11/06 (2013.01); C07F 3/003 (2013.01); C07F 3/06 (2013.01); H01L 51/0092 (2013.01); H05B 33/14 (2013.01); H05B 33/22 (2013.01); C09K 2211/186 (2013.01); H01L 51/5012 (2013.01)

(58) Field of Classification Search
CPC ....................................................... C09K 11/06
USPC ........................................................ 546/152
See application file for complete search history.

(56) References Cited

U.S. PATENT DOCUMENTS

| | | | |
|---|---|---|---|
| 4,539,507 | A | 9/1985 | Van Slyke |
| 4,720,432 | A | 1/1988 | Van Slyke |
| 2007/0072001 | A1 | 3/2007 | Tsuboyama |
| 2007/0072003 | A1 | 3/2007 | Ise |
| 2009/0078317 | A1 | 3/2009 | Kim |
| 2010/0152455 | A1 | 6/2010 | Kim |

FOREIGN PATENT DOCUMENTS

| | | | |
|---|---|---|---|
| EP | 1923448 | 5/2008 | |
| EP | 2053112 | 4/2009 | |
| EP | 2062900 | 5/2009 | |
| GB | 2376691 | 12/2002 | |
| JP | 08-301877 | 11/1996 | |
| JP | 09268284 | * 10/1997 | ............ C09K 11/06 |
| JP | 9328678 | 12/1997 | |
| KR | WO 2008082249 | * 6/2008 | ............ C09K 11/06 |
| KR | WO 2008/082249 | * 7/2008 | ............ C09K 11/06 |
| PL | 385938 | 3/2010 | |
| WO | 00/58315 | 10/2000 | |
| WO | 2004073030 | 8/2004 | |
| WO | 2008/082249 | 7/2008 | |

OTHER PUBLICATIONS

Ishiko et al. Abstract of JP 02008290, STN Accession No. 1991:14673 ZCAPLUS Document No. 114:14673.*
Boersma, Journal of Organometallic Chemistry, 1968, 13(2), 291-9.*
Boersma et al. Journal of Organometallic Chemistry (1968), 13(2), 291-9.*
Tanasescu et al. STN Accession No. 1986:139067, Abstract of RO 86062.*
Ballardini, Roberto et al., (1986) Phosphorescent 8-quinolinol metal chelates. Excited-state properties and redox behavior. Inorg Chem 25(22):3858-3865.
Bhatnagar, Dinesh C. and Forster, Leslie S. (1965) The luminescence of oxines and metal oxinates. Spectochim Acta 21(10):1803-1807.
Chen, C. H. and Shi, Jianmin (1998) Metal chelates as emitting materials for organic electroluminescence. Coord Chem Rev 171:161-174.
Colle, Michael et al., (2002) The structure of the blue luminescent δ-phase of tris(8-hydroxyquinoline)aluminium(III) (Alq3). Chem Commun 2908-2909.
Hopkins, T. A. et al., (1996) Substituted Aluminum and Zinc Quinolates with Blue-Shifted Absorbance/Luminescence Bands: Synthesis and Spectroscopic, Photoluminescence, and Electroluminescence Characterization. Chem Mater 8 (2):344-351.

(Continued)

Primary Examiner — Nizal Chandrakumar
(74) Attorney, Agent, or Firm — Rodney J. Fuller; Booth Udall Fuller, PLC

(57) ABSTRACT

This invention relates to compounds of general formula $(R')_xZn_y(L)_z(A)_n(XR)_m$, where L is a bi- or multifunctional organic neutral ligand or its deprotonated form, containing at least two heteroatoms selected from N, O, S, wherein at least one of the functional groups of the ligand is selected from —OH, —SH, —NH$_2$, —NHR, —COOH, —CONH$_2$, —CONRH or their deprotonated equivalents; A is an inorganic anion, X is oxygen or sulfur, R' is C1-C10 alkyl, straight or branched, benzyl, phenyl cyclohexyl or halogen, R is hydrogen, alkyl or aryl, x is a number from 0 to 6, y is a number from 1 to 12, z is a number from 1 to 12, n is a number from 0 to 6, m is a number from 0 to 6, wherein x≠0, n≠0 and m≠0 at the same time and if n and m=0, then x≠z. The invention also relates to the method of preparation of these compounds and applications thereof.

5 Claims, 3 Drawing Sheets

(56) References Cited

OTHER PUBLICATIONS

Sapochak, Linda S. et al., (2002) Electroluminescent Zinc(II) Bis(8-hydroxyquinoline): Structural Effects on Electronic States and Device Performance. J Am Chem Soc 124(21):6119-6125.

Tang, C. W. and Vanslyke, S. A. (1987) Organic electroluminescent diodes. Appl Phys Lett 51(12):913-915.

Wang, Lei et al., (2012) A novel decanuclear Co(II) cluster with adamantane-like metallic skeleton supported by 8-hydroxyquinoline and in situ formed CO3(2-) anions. Dalton Trans 41(20):6242-6246.

ISR of PCL/PL2011/000070 mailed Oct. 24, 2011.

Hong-Yan (2008) The synthesis and crystal structures of new 2-aminomethylbenzimidazole Zinc (II) complexes exhibiting luminescence. Transition Metal Chemistry 33(1): 9-15.

Paira et al., (2007) Zn(II), Cd(II) and Ha(II) complexes of 8-aminoquinoline, Structure, spectra and photoluminescence property. Polyhedron 26(15): 4131-4140.

\* cited by examiner

LUMINESCENT COMPOUNDS, METHOD OF PREPARATION OF LUMINESCENT COMPOUNDS AND APPLICATIONS THEREOF

RELATED APPLICATION DATA

This application is the U.S. National Stage of International Application No. PCT/PL2011/000070, filed Jul. 6, 2011, which claims priority to Polish Patent Application No. P.391776 filed Jul. 7, 2010, the contents of each of which are herein expressly incorporated by reference for all purposes.

The invention relates to luminescent compounds based on complexes of organic ligands with zinc, with potential application in electronics, biology and medicine and, in particular, in the design of organic light emitting diodes The invention also relates to the method of preparation of these compounds and applications thereof.

8-hydroxyquinoline (Hq) chelates of type $Mq_n$ (where M is metal) are widely used in analytical chemistry. As of 1980s, extensive research has started regarding the usefulness of Hq chelates and their derivatives in the design of emission and conduction layers in the production of organic light emitting diodes (OLEDs). A true milestone in material chemistry that led to preparation of first stable electroluminescent diodes was the use of trichelate complex of 8-Hq with aluminum ($Alq_3$). [C. W. Tang, S. A. VanSlyke *Appl. Phys. Lett.*, 1987, 51, 913 and patents no. 1985 U.S. Pat. No. 4,539,507 and 1988 U.S. Pat. No. 4,720,432]. In recent years, extensive research was also conducted on electroluminescence properties of bischelate 8-Hq complexes of zinc ($Znq_2$) [L. S. Sapochak, F. E. Benincasa, R. S. Schofield, J. L. Baker, K. K. C. Riccio, D. Fogarty, H. Kohlmann, K. F. Ferris, P. E. Burrows *J. Am. Chem. Soc.*, 2002, 124, 6119]

In the structure of $Alq_3$, the aluminum atom is bound to three deprotonated hydroxyquinoline ligands. Thermal stability of $Alq_3$ makes it possible to deposit the compound in thin layers without decomposition by vacuum planting at 350° C. Quantum yield of $Alq_3$ in solutions was 11% with maximum fluorescence at 532 nm. $Znq_2$ is characterized by comparable quantum yield. [T. A. Hopkins, K. Meerholz, S. Shaheen, M. L. Anderson, A. Schmidt, B. Kippelen, A. B. Padias, H. K. Hall, Jr., N. Peyghambarian, N. R. Armstrong *Chem. Mater.*, 1996, 8, 344]

Various attempts are made to obtain materials with pre-defined color of the emitted light. This is particularly important in the design of OLEDs of potential use e.g., in TV panels. Currently, extensive studies are conducted to obtain fluorescent systems with a wide range of colors, with blue and white emitters being probably the most attractive.

There is also a need to search for novel possibilities of fluorescent tagging, widely used in imaging and physico-chemical examinations in biology and medicine. The area of applicability of fluorescent tags is very wide and diverse. They are used in studying and imaging of cell components: the membrane, cytoskeletal proteins, organelles: nuclei, mitochondria, lysosomes, endoplasmic reticula, Golgi apparata; tags are used to stain proteins for various purposes, including staining antibodies and enzymes, peptides, oligonucleotides and nucleic acids; fluorescent tags of suitable designs are used as chemical sensors for the measurement of concentrations of important intracellular substances, such as $O_2$, $K^+$, $H^+$ and for the measurement of electric potentials of cellular membranes; tagged substances are used in both in vitro and in vivo studies, both in fixed materials and in living models. Tagged substances are used in many areas of biology and medicine, including genetics, biochemistry, e.g. in studying enzymatic activity, immunology, pathology, neurology, medical diagnostics, etc. In cellular function studies, tagging is used to study cell viability, cellular cycle, adhesion, apoptosis, substance cytotoxicity tests, etc. Numerous modern study techniques and technologies widely used in the above areas make use of compounds containing fluorescent tags, and the advances in the development of these techniques is determined by the advances in the development of tags, in particular in their sensitivity and stability. These techniques include: flow cytometry; biochips; DNA sequencing or nucleic acid synthesis by polymerase chain reaction (PCR); fluorescence correlation spectroscopy (FCS) used for studying intermolecular interactions, including interbiomolecular interactions, where high intensity excitation radiation is also used and where the intensity of the luminescence of the tag following the capture of individual photons; Fluorescence Resonance Energy Transfer (FRET)-based biological sensors, which are widely used in cellular biology for studying signaling pathways and for imaging of biological processes using confocal fluorescence lifetime imaging microscopy (FLIM)—an imaging technique based on measuring the differences in the lifetimes of fluorescence used to study protein-protein interactions and limited by the low quantum yield of currently used fluorophores; or super-resolution stimulated emission depletion (STED) microscopy used for do studying subcellular location of proteins (resolution of ca. 70 nm).

The market of fluorescent tags is comprised of fluorescent proteins, small organic molecules and quantum dots, which have been introduced in recent years and which are still in the implementation stage [1, 2, 4, 5]. In addition, literature contains reports on attempted preparation of tags based on phosphorescent lanthanide complexes [10], carbon nanoparticles [9] and complexes of heavy metals [11]. The predominant and the most versatile group are small organic molecules. They belong to various classes of compounds, their molecular mass usually does not exceed 1000 Da, and their size allows them to be inscribed within a sphere of the diameter of 1-1.5 nm. Quantum dots (QDs), or semiconductor-based nanoparticles, have photoluminescent properties, and their diameter usually does not exceed 10 nm. An example of QDs are nanoparticles of cadmium selenide coated in a zinc sulphide layer: CdSe/ZnS QDs. Organic tags are small, but not resistant to photobleaching. Quantum dots are optically stable, but too large for many applications.

In the case of complexes based on Hq and its derivatives, the shift of maximum fluorescent emission may be achieved by introduction of a ligand with modified electronic properties, a change in the metal center or in the geometry of complex coordination zone. For example, maximum fluorescence for $Alq'_3$ (i.e., a complex consisting of monoanions of 8-hydroxyquinoline substituted with —$CH_3$ at C-4) is 515 nm and is shifted hypsochromatically by 17 nm compared to $Alq_3$.

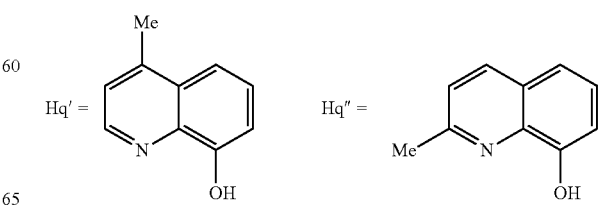

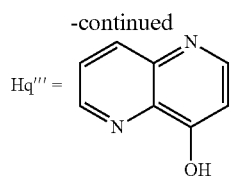

On the other hand, the use of 8-hydroxyquinoline substituted with —$CH_3$ at C-2 led to formation of a poorly stable oxoaluminum complex of the type [(q"Al)$_2$O], with the maximum light emission at 490 nm. When a Hq''' proligand was used, an Al(q''')$_3$ compound was obtained with fluorescence spectrum peak at 440 nm. [C. H. Chen, J. Shi *Coordin. Chem. Rev.*, 1998, 171, 161]

Fluorescent properties of complexes of the type $Mq_n$ depend also on the nature of the central ion:
i) chelate complexes with paramagnetic metal ions do not show any fluorescence (e.g., Cr, Ni complexes);
ii) quantum yield drops are usually observed along with the increase in the atomic number of metal ions;
iii) fluorescence maximum is shifted toward longer wavelengths along with the increasingly covalent character of the metal-ligand bond; for instance, Al, Ga, In chelates emit light at 532, 545 and 558 nm, respectively, while $Mgq_2$ emits light of shorter wavelengths (500 nm) than that of its zinc analog $Znq_2$ (557 nm).

[D. C. Bhatnagar, L. S. Forster *Spectrochim. Acta*, 1965, 21, 1803; R. Ballardini, G. Varani, M. Y. Indelli, F. Scandola *Inorg. Chem.*, 1986, 25, 3858]

The shift in the emission bands is also dependent on the geometry of the molecule, as well as relative locations of molecules in the crystalline lattice and intermolecular interactions. For instance, differences in spectroscopic properties are observed for different polymorphic variants of $Alq_3$. [M. Cölle, R. E. Dinnebier, W. Brüning *Chem. Commun.*, 2002, 2908]

The described examples pertain mostly to mononuclear chelate compounds containing ligands of one type, which leads to small diversity in the molecular geometries and crystal packing and, thus, in their spectroscopic properties.

The aim of the invention was to obtain a novel class of fluorescent materials expanding the possibilities for the design of modern fluorescent systems.

The subject matter of the invention are novel compounds of general formula $(R')_xZn_y(L)_z(A)_n(XR)_m$, where L is a bi- or multifunctional organic neutral ligand or its deprotonated form, containing at least two heteroatoms selected from N, O, S, wherein at least one of the functional groups of the ligand is selected from —OH, —SH, —$NH_2$, —NHR, —COOH, —$CONH_2$, —CONRH or their deprotonated equivalents; A is an inorganic anion, R' is C1-C10 alkyl, straight or branched, benzyl, phenyl, cyclohexyl or halogen, X is oxygen or sulfur, R is hydrogen, alkyl or aryl, x is a number from 0 to 6, y is a number from 1 to 12, z is a number from 1 to 12, n is a number from 0 to 6, m is a number from 0 to 6, wherein x≠0, n≠0 and m≠0 at the same time and if n and m=0, then x≠z.

Preferably, the inorganic anion A is an anion originating from an oxyacid, a binary acid, an acid anhydride, oxygen, sulfur, selenium, or tellurium.

More preferably, the inorganic anion A is $O^{2-}$, $S^{2-}$, $Se^{2-}$, $Te^{2-}$, $CO_3^{2-}$, $SO_4^{2-}$, $SO_3^{2-}$, $CS_2O^2$, $CS_3^{2-}$, $BO_3^{3-}$, $NO_2^-$, $NO_3^-$.

Most preferably, the inorganic anion A is $O^{2-}$, $S^{2-}$, $Se^{2-}$, $CO_3^{2-}$, $CS_2O^{2-}$, $BO_3^{3-}$, $NO_3^-$.

Preferably, the multifunctional ligand L consists of a neutral organic compound or its deprotonated equivalent containing at least one Lewis base center and at least one functional group selected from —OH, —SH, —$NH_2$, —NHR, —COOH, —$CONH_2$, —CONRH or their deprotonated equivalents.

More preferably, the multifunctional ligand L consists of an organic compound containing at least one Lewis base center and at least one functional group selected from —$O^-$, —$S^-$, —$NH^-$, —$NR^-$, —$COO^-$, —$CONH^-$, —$CONR^-$.

Preferably, the multifunctional ligand L consists of an organic compound in which the Lewis base center is separated from the —OH, —SH, —$NH_2$, —NHR, —COOH, —$CONH_2$, —CONRH group by a saturated or unsaturated carbon chain of 1-3 carbon atoms.

More preferably, the multifunctional ligand L consists of an organic compound in which the Lewis base center is separated from the —$O^-$, —$S^-$, —$NH^-$, —$NR^-$, —$COO^-$, —$CONH^-$, —$CONR^-$ group by a saturated or unsaturated carbon chain of 1-3 carbon atoms.

Preferably, the ligand L is the organic compound of formula 1 or of formula 2 or of formula 3 or of formula 4 or of formula 5 or of formula 6 or of formula 7 or of formula 8 or of formula 9 or of formula 10 or of formula 11 or of formula 12 or of formula 13:

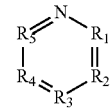

Formula 1

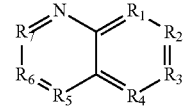

Formula 2

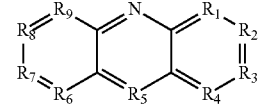

Formula 3

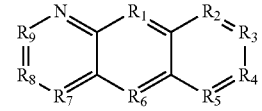

Formula 4

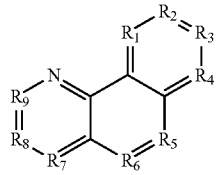

Formula 5

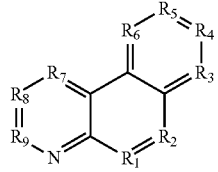

Formula 6

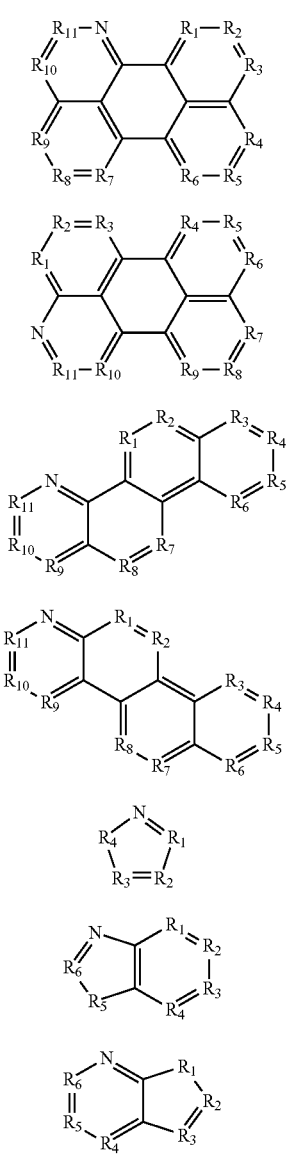

Formula 7

Formula 8

Formula 9

Formula 10

Formula 11

Formula 12

Formula 13 wherein R1, R2, R3, R4, R5, R6, R7, R8, R9, R10, R11 are heteroatoms selected from nitrogen, sulfur, oxygen or carbon atom attached to a hydrogen, straight or branched C1-C10 alkyl (possibly substituted), phenyl (possibly substituted) benzyl (possibly substituted), ether group (possibly substituted), ketone group (possibly substituted), halogen, —OH, —SH, —NH$_2$, —NHR, —COOH, —CONH$_2$, —CONRH, —O$^-$, —S$^-$, —NH$^-$, —NR$^-$, —COO$^-$, —CONH$^-$, —CONR$^-$ wherein R1 is preferably a carbon atom attached to one of the groups: —OH, —SH, —NH$_2$, —NHR, —COOH, —CONH$_2$, —CONRH, more preferably a carbon atom attached to one of the groups: —O$^-$, —S$^-$, —NH$^-$, —NR$^-$, —COO$^-$, —CONH$^-$, —CONR$^-$.

The invention also relates to the method for preparation of compounds of general formula $(R')_x Zn_y(L)_z(A)_n(XR)_m$, where the precursor $R'_x(Zn_y(L)_z(X_kR)_m$, where L is a bi- or multifunctional organic neutral ligand or its deprotonated form, containing at least two heteroatoms selected from N, O, S, wherein at least one of the functional groups of the ligand is selected from —OH, —SH, —NH$_2$, —NHR, —COOH, —CONH$_2$, —CONRH or their deprotonated equivalents; X is oxygen or sulfur, R' is C1-C10 alkyl, straight or branched, benzyl, phenyl cyclohexyl or halogen, R is hydrogen, alkyl or aryl, x is a number from 0 to 6, y is a number from 1 to 12, z is a number from 1 to 12, m is a number from 0 to 6, k is 1 or 2, is subjected to reaction with oxygen or water or elemental sulfur or selenium, or tellurium, or oxyacids or binary acids, or acid anhydrides and/or inorganic acid salts in a solvent or to thermal transformation.

The method of the invention allows for using anhydrous organic solvents, organic solvents containing water as well as inorganic solvents, preferably water.

Preferably, the organic solvent is toluene, tetrahydrofuran, hexane, methylene chloride, dimethylsulfoxide, acetonitrile as well as an alcohols, phenol or acids in which the precursor is well soluble or a mixture of these compounds.

Reactions with oxygen may be conducted with oxygen, atmospheric air or mixtures of both as oxidating agents.

Preferably, an acid anhydride is used in the reaction.

Preferably, the acid anhydrides used include $CO_2$, $SO_2$, $CS_2$, $B_2O_3$, NO, $NO_2$.

Preferably, inorganic acid salts are used in the reaction.

Preferably, the inorganic salts used include the salts of carbonic acid, sulfuric (IV) acid sulfuric (VI) acid, thiocarbonic acid, boric acid, nitric (III) acid, nitric (V) acid, hydrosulphuric acid, hydroselenic acid, hydrotelluric acid.

Preferably, oxyacids used include carbonic acid, sulfuric (IV) acid sulfuric (VI) acid, thiocarbonic acid, boric acid, nitric (III) acid, nitric (V) acid.

Preferably, the binary acids used include $H_2S$, $H_2Se$, $H_2Te$.

Preferably, elemental sulfur, selenium or tellurium is used in the reaction.

Preferably, the reaction is conducted in the temperature range of −70-200° C., more preferably −70-100° C. and in the pressure range of 0.1-100 bar, more preferably 1-100 bar, and most preferably 1-20 bar.

Preferably, thermal transformation is conducted in the temperature range of 60-700° C., more preferably 60-400° C.

The invention also relates to the use of compounds of general formula $(R')_x Zn_y(L)_z(A)_n(XR)_n$, for manufacture of emission and conduction layers for use in organic electroluminescent diode production technology as well as in other devices making use of luminophores.

Compounds of the invention may also be used as fluorescent tags in cellular and tissue imaging.

The method of the invention allows for convenient preparation of novel classes of fluorescent materials characterized by the presence of at least two types of ligands, various nuclearity and various quantitative metal-ligand ratios, which in turn affects relative locations of ligands, geometry of complexes and thus the packing of the molecules in the crystal lattice. Such changes lead to significant changes towards more desirable spectroscopic properties of the obtained materials, allowing for rational design of novel fluorescent systems. For example, peak fluorescence of the $Zn_{10}q_{12}(CO_3)_4$ complex is located at 490 nm and is blue-shifted by 60 nm compared to classic chelates of aluminum and zinc. In addition, a 6-fold increase in quantum yield (11% to 64%) is observed for $Zn_{10}q_{12}(CO_3)_4$ compared to classic compounds.

The new method extends the possibilities for preparing fluorescent compounds with predefined crystallographic structures and unique spectroscopic properties.

Compounds according to the invention will find their use in the imaging of cells and tissues in biology and medicine, particularly as fluorescent tags. This application makes use of their capability to register the emission of light with very high intensity, sometimes down to a single emitted photon. Such level of sensitivity is unattainable in case of light absorption-based spectroscopic techniques. Compounds of the invention used as fluorescent tags are significantly smaller than quantum dots and, at the same time, much more resistant to photobleaching than organic dyes.

Before or upon use, compounds of the invention used for the imaging of cells and tissues will be tethered, either covalently or by physical interactions, to molecules originating from cells, their synthetic copies or analogs, in particular to proteins, peptides, nucleic acids, nucleosides, nucleotides, polysaccharides, hormones, amino acids or with other molecules, in particular drugs or toxins, where said tethering of the compounds of the invention will be performed with a view to the proven or suspected interaction of these compounds with one of the aforementioned molecules, i.e. molecules originating from cells, their synthetic copies or analogs, in particular to proteins, peptides, nucleic acids, nucleosides, nucleotides, polysaccharides, hormones, amino acids. As part of this application, compounds of the invention will also be used in qualitative or quantitative analysis of chemical substances in tissues or cells performed in vitro or in vivo, either in living models or in fixed materials. Finally, the compounds of the invention will be used due to their ability to accumulate in tissues, cells or cell fragments.

The comparison of the known parameters of the compound according to the invention of the formula $[Zn(CO_3)]_4[Znq_2]_6$, such as its size, quantum yield, Stokes shift, and optical stability with the parameters of fluorescent tags currently available in, the market, listed in Table 1 suggests that the compound according to the invention has a significant advantage over the tags of current art and that it may significantly expand the area of applicability of fluorescent tags.

BRIEF DESCRIPTION OF THE DRAWINGS

The present invention will be understood and appreciated more fully from the following detailed description taken in conjunction with the appended figures:

FIG. 3 shows fluorescence microscopy image of the stained fibroblasts.

Figure 1:
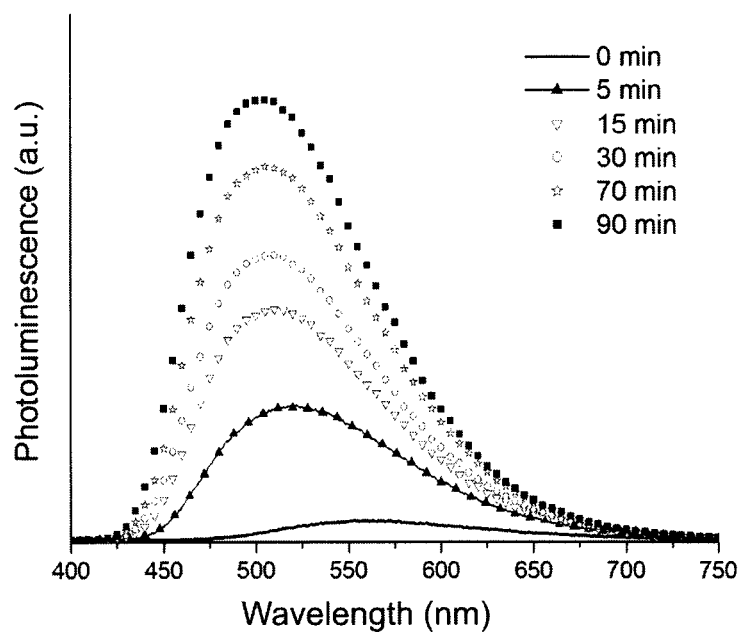
FIG. 1: shows the increase in fluorescence intensity as measured in the course of transformation of $[(Znq_2)_2(tBuZnOH)_2]$ to $Zn_{10}q_{12}(CO_3)_4$ in the presence of carbon dioxide.

The subject matter of the invention is presented in more detail in the following examples.

EXAMPLE 1

Preparation of a Fluorescent Compound of Formula $[(Znq_2)_2(tBuZnOH)_2]$

10 μL of water (0.56 mmol $H_2O$) was added to 5 mL of a solution containing 0.15 g (0.56 mmol) of tert-butylzinc derivative of $(tBuZnq)_3$ in tetrahydrofuran. The reaction was carried out for 12 hours at room temperature. Crystallization yielded monocrystals suitable for x-ray structural studies. The x-ray structural studies showed that the product of the reaction was the $[(Znq_2)_2(tBuZnOH)_2]$ adduct of structural formula presented below.

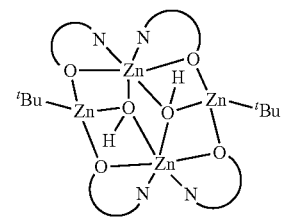

EXAMPLE 2

Preparation of a Fluorescent Compound of Formula $[(Znq_2)_2(EtZnOH)_2]$

10 μL of water (0.56 mmol $H_2O$) was added to 5 mL of a solution containing 0.135 g (0.56 mmol) of ethylzinc derivative of $(EtZnq)_2$ in tetrahydrofuran. The reaction was carried out for 4 hours at room temperature. The x-ray structural and spectral studies showed that the product of the reaction was the $[(Znq_2)_2(EtZnOH)_2]$ adduct of structural formula presented below.

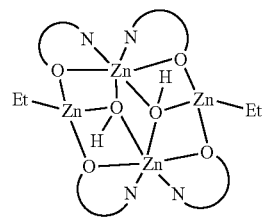

EXAMPLE 3

Preparation of a Fluorescent Compound of Formula $[(tBu)_2Zn_4(\mu_4-O)(Meq)_4]$ 0.1 mL of 0.5M solution of water in THF (0.05 mmol $H_2O$) was added to 5 mL of a solution containing 0.150 g (0.5 mmol) of tert-butylzinc derivative of 5,7-dimethyl-8-hydroxyquinoline $(tBuZnMeq)_3$ in tetrahydrofuran. The reaction was carried out for 4 hours at room temperature. Crystallization yielded monocrystals suitable for x-ray structural studies. The x-ray structural studies showed that the product of the reaction was the $[(tBu)_2Zn_4(\mu_4-O)(Meq)_4]$ adduct of structural formula presented below

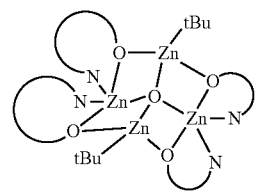

EXAMPLE 4

Preparation of a Fluorescent Compound of Formula
[($^t$Bu)$_2$Zn$_4$(μ$_4$-O)(Meq)$_4$]

The monocrystals of the [(ZnMeq$_2$)$_2$($^t$BuZnOH)$_2$] adducts were heated at 200° C. for 60 min. After this time, crystalline powder was obtained and characterized using an x-ray powder diffractometer. The spectrum of the tested compound corresponds to the reference spectrum of the [$^t$Bu)$_2$Zn$_4$(μ$_4$-O)(Meq)$_4$] adduct of structural formula presented in Example 3.

EXAMPLE 5

Preparation of a Fluorescent Compound of Formula
[($^t$Bu)$_2$Zn$_4$(μ$_4$-O)(Meq)$_4$]

The monocrystals of the [(ZnMeq$_2$)$_2$($^t$BuOOZnMeq)$_2$] adducts were heated at 200° C. for 30 min. After this time, crystalline powder was obtained and characterized using an x-ray powder diffractometer. The spectrum of the tested compound corresponds to the reference spectrum of the [($^t$Bu)$_2$Zn$_4$(μ$_4$-O)(Meq)$_4$] adduct of structural formula presented in Example 3.

EXAMPLE 6

Preparation of a Fluorescent Compound of Formula
[($^i$Pr)$_2$Zn$_4$(μ$_4$-O)(Meq)$_4$)]

0.1 mL of 0.5M solution of water in THF (0.05 mmol H$_2$O) was added to 5 mL of a solution containing 0.135 g (0.5 mmol) of isopropyl derivative of 5,7-dimethyl-8-hydroxyquinoline ($^i$PrZnMeq)$_3$ in tetrahydrofuran. The reaction was carried out for 4 hours at room temperature. The x-ray structural and spectral studies showed that the product of the reaction was the [($^i$Pr)$_2$Zn$_4$(μ$_4$-O)(Meq)$_4$] adduct of structural formula presented below.

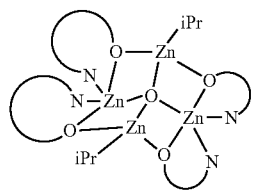

EXAMPLE 7

Preparation of a Fluorescent Compound of Formula
[(Et)$_2$Zn$_4$(OEt)$_2$(Bq)$_4$]

2 mL of the solution containing 0.1 g of the ethylzinc derivative of 10-hydroxybenzoquinoline ($^t$BuZnBq)$_3$ in tetrahydrofuran was submitted to reaction with oxygen at −70° C. for 5 minutes. Crystallization yielded monocrystals suitable for x-ray structural studies. The x-ray structural studies showed that the oxidation product was the [(Et)$_2$Zn$_4$(OEt)$_2$(Bq)$_4$] adduct of structural formula presented below.

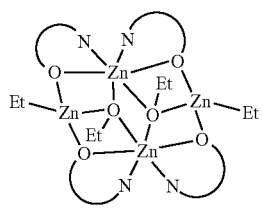

EXAMPLE 8

Preparation of a Fluorescent Compound of Formula
{[Zn(BTZ)$_2$] ($^t$BuZnBTZ)$_2$}

An equimolar amount of water was added to 5 mL of the solution containing 0.1 g of tert-butylzinc derivative of 2-(2-hydroxyphenyl)benzothiazole (BTZ) in toluene at −78° C. The reaction mixture was left to reach the room temperature, after which the reaction was conducted for 4 hours. Crystallization yielded monocrystals suitable for x-ray structural studies. The x-ray structural studies showed that the product of the reaction was the {[Zn(BTZ)$_2$] ($^t$BuZnBTZ)$_2$} adduct of structural formula presented below.

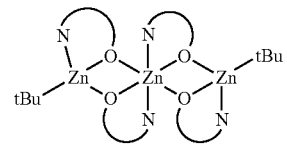

EXAMPLE 9

Preparation of a Fluorescent Compound of Formula
Zn$_{10}$q$_{12}$(CO$_3$)$_4$ 5 mL of the solution containing 0.1 g of the precursor [(Znq$_2$)$_2$($^t$BuZnOH)$_2$] in tetrahydrofuran was submitted to reaction with carbon dioxide at 0° C. under 1 atm. Crystallization yielded monocrystals suitable for x-ray structural studies. The x-ray structural studies showed that the product of the reaction was the Zn$_{10}$q$_{12}$(CO$_3$)$_4$ adduct of structural formula presented below.

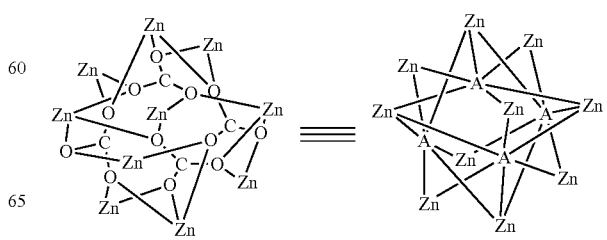

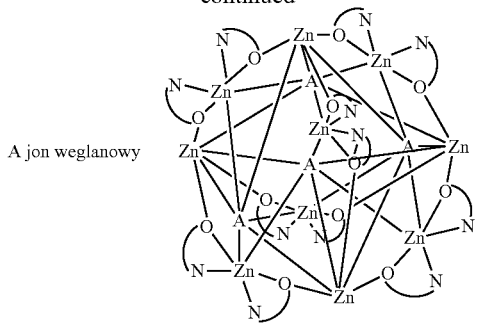

A jon weglanowy

EXAMPLE 10

Preparation of a Fluorescent Compound of Formula $Zn_{10}q_{12}(CO_3)_4$ 5 mL of the solution containing 0.1 g of the precursor $[(Znq_2)_2(^tBuZnOH)_2]$ in tetrahydrofuran was submitted to reaction with carbon dioxide at 25° C. under 70 atm for 2 h. The product was obtained as a crystalline powder characterized using an x-ray powder diffractometer. The x-ray diffraction studies showed that the product of the reaction was the $Zn_{10}q_{12}(CO_3)_4$ adduct of structural formula presented in Example 9.

EXAMPLE 11

Preparation of a Fluorescent Compound of Formula $Zn_{10}q_{12}(CO_3)_4$ 0.042 g (0.4 mmol) of $Na_2CO_3$. was added to 5 mL of a solution containing 0.355 g (1 mmol) $Znq_2$ precursor in toluene. The reaction was carried out at 25° C. for 24 h. Crystallization yielded monocrystals suitable for x-ray structural studies. The x-ray diffraction studies showed that the product of the reaction was the $Zn_{10}q_{12}(CO_3)_4$ adduct of structural formula presented in Example 9.

Figure 2:
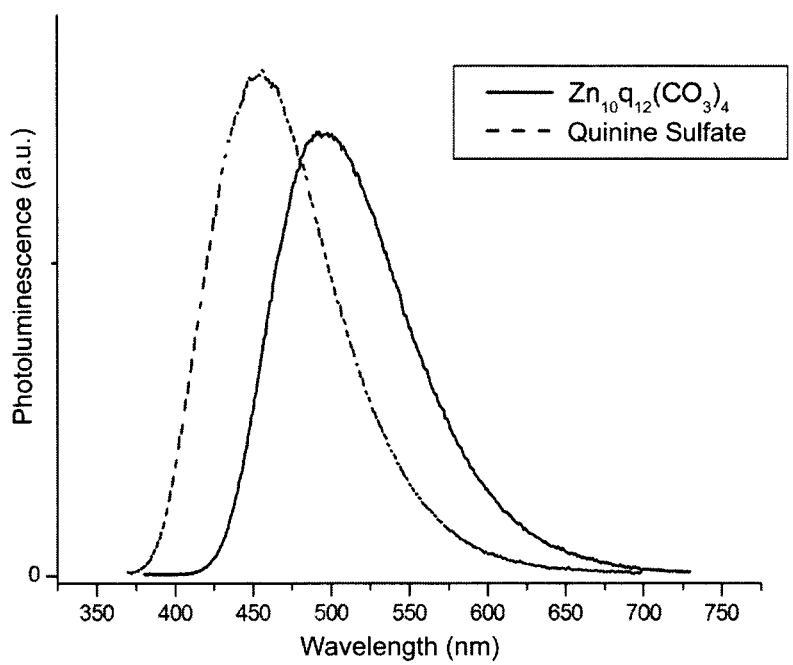
FIG. 2: shows the fluorescence spectra of $Zn_{10}q_{12}(CO_3)_4$ (solid line) and quinine sulphate as the reference compound (dashed line) in toluene.

Spectroscopic properties of $Zn_{10}q_{12}(CO_3)_4$ obtained according to Examples 9, 10 and 11 are presented in FIG. 1 and FIG. 2. FIG. 1 shows the increase in fluorescence intensity as measured in the course of transformations of the $[(Znq_2)_2(^tBuZnOH)_2]$ precursor in the presence of carbon dioxide, while FIG. 2 shows the fluorescence spectra of $Zn_{10}q_{12}(CO_3)_4$ (solid line) and quinine sulphate as the reference compound (dashed line) in toluene. Quantum yield of $Zn_{10}q_{12}(CO_3)_4$ is 64% (Examples 9, 10 and 11).

Table 2 presents crystallographic data of $[(^tBu)_2Zn_4(\mu_4\text{-}O)(Meq)_4]$, $[(^tBu)_2Zn_4(\mu_4\text{-}O)(Meq)_4]$, $[(Et)_2Zn_4(OEt)_2(Bq)_4]$, $\{[Zn(BTZ)_2](^tBuZnBTZ)_2\}$ and $Zn_{10}q_{12}(CO_3)_4$.

EXAMPLE 12

Figure 3:
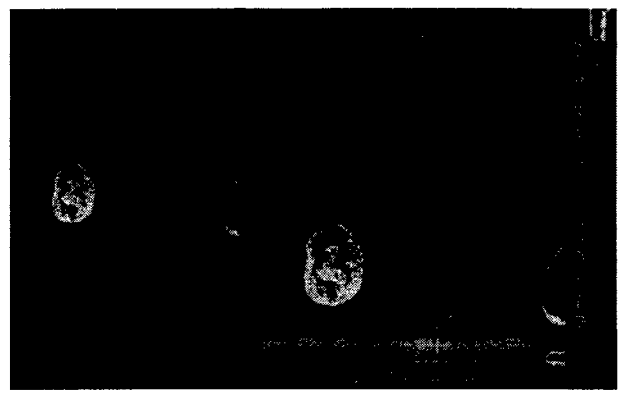
FIG. 3: $Zn_{10}q_{12}(CO_3)_4$, solubilized in water and double- and triple-block polymers, was used for staining a line of a human fibroblasts.
Figure 4:
FIG. 4: shows fluorescence microscopy image of a control sample, i.e., cells treated with polymer alone.

Cell Staining $Zn_{10}q_{12}(CO_3)_4$, solubilized in water using appropriate double- and triple-block polymers, such as polyethylene-polypropylene glycol and poloxameres, was used for staining of a line of human fibroblasts. Microscopic specimens were prepared following three hours of incubation of cells in a phosphate buffer solution containing $Zn_{10}q_{12}(CO_3)_4$. Microscopic analysis revealed efficient migration of the fluorophore into the cytoplasm, resulting in cell staining. No drop of fluorescence intensity over time was observed during irradiation with excitation wavelengths. Polymer-coated molecules dissolved in water had the average size of ca. 5 nm. FIG. 3 shows a fluorescence microscopy image of stained fibroblasts, while FIG. 4 shows an image of the control sample, i.e. cells treated with polymer alone.

EXAMPLE 13

Figure 5:
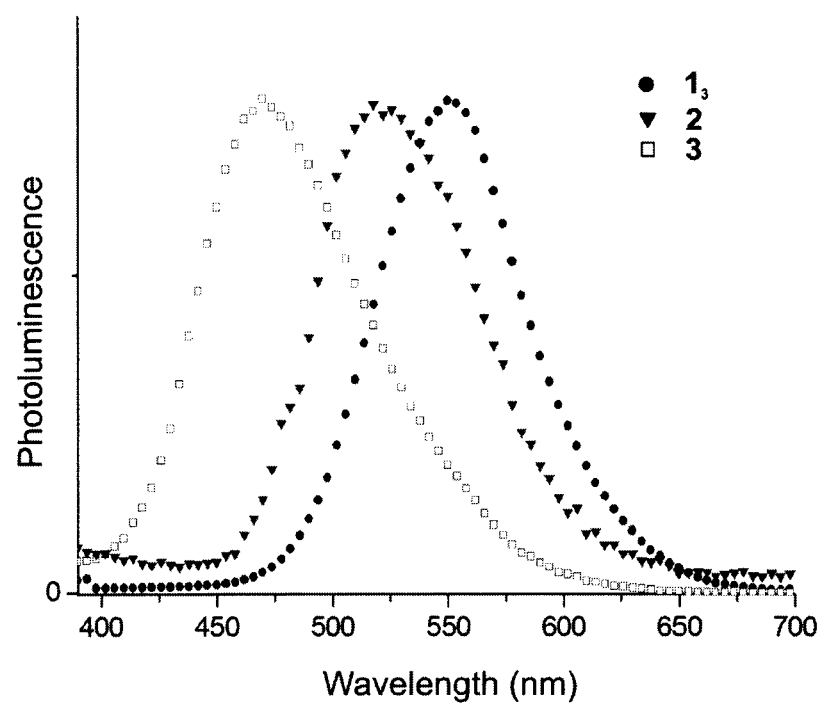
FIG. 5: depicts luminescence bands of $[RZn(q)]_3$ ($1_3$), $[(R)_3Zn_5(\mu_4-O)(q)_5]$ (2) and $[Zn(q)_2]_2[RZn(OH)]_2$ (3).

Thin layers of $[RZn(q)]_3$ ($1_3$), $[(R)_3Zn_5(\mu_4\text{-}O)(q)_5]$ (2) and $[Zn(q)_2]_2[RZn(OH)]_2$ (3) were obtained. The compounds have different spectroscopic properties. Maximum luminescence bands cover a wide range of 470 nm to 555 nm (FIG. 5), which makes it possible to obtain emission layers generating blue, green, or yellow light.

TABLE 1

| Parameter | Fluorescent organic dyes | Quantum dots (QDs) | $[Zn(CO_3)]_4[Znq_2]_6$ |
|---|---|---|---|
| Absorption spectrum | Band spectrum with half-width ranging from 20 to over 100 nm. | Continuous spectrum, with intensities increasing towards shorter wavelengths (UV), which makes excitation of QDs possible over a wide range of the spectrum. | Band spectrum with half-width ranging from 80 to 200 nm which makes excitation possible over a wide range of the spectrum. |
| Emission spectrum | Asymmetric bands with half-widths of 30-100 nm | Symmetric bands with half-widths of 30-90 nm | Symmetric bands with half-widths of 50-200 nm |
| Stokes shift | Usually below 50 nm | Below 50 nm upon excitation with visible wavelengths. | Above 100 nm, which makes the emitted light have a different color than the excitation light. |
| Quantum yield (QY) | 0.5-1.0 | 0.1-0.5 | Above 0,5 |
| Size | Ca. 0.5-10 nm | 10-60 nm, (hydrodynamic radius) | 1.5-5 nm, (hydrodynamic radius) |

TABLE 1-continued

| Parameter | Fluorescent organic dyes | Quantum dots (QDs) | $[Zn(CO_3)]_4[Znq_2]_6$ |
|---|---|---|---|
| Optical stability | Insufficient for methods making use of high-intensity light or near-infrared tags Application in long-lasting tests is impossible. Photobleaching occurs. | Orders of magnitude higher than in case of organic tags. Blinking occurs. | Very high optical stability allowing to conduct tests lasting many hours. No photobleaching or blinking. |

TABLE 2

Crystallographic data of $[(^tBu)_2Zn_4(\mu_4\text{-}O)(Meq)_4]$, $[(^tBu)_2Zn_4(\mu_4\text{-}O)(Meq)_4]$, $[Et_2Zn_4(OEt)_2(Bq)_4]$, $\{[Zn(BTZ)_2](^tBuZnBTZ)_2\}$ and $Zn_{10}q_{12}(CO_3)_4$

| | $[(^tBu)_2Zn_4(\mu_4\text{-}O)(Meq)_4]$ Example 1 | $[(^tBu)_2Zn_4(\mu_4\text{-}O)(Meq)_4]$ Example 3 |
|---|---|---|
| molecular formula | $C_{44}H_{42}N_4O_6Zn_4$ | $C_{52}H_{58}N_4O_5Zn_4$ |
| $M_r$ | 984.30 | 1080.50 |
| crystallographic system | Triclinic | triclinic |
| space group | P-1 (no. 2) | P-1 (no. 2) |
| temperature [K] | 100 (2) | 100 (2) |
| a [Å] | 11.3576 (7) | 13.4530 (13) |
| b [Å] | 11.7735 (6) | 13.7190 (15) |
| c [Å] | 12.1176 (7) | 18.322 (2) |
| α [°] | 96.619 (3) | 97.862 (5) |
| β [°] | 106.962 (3) | 96.991 (7) |
| γ [°] | 109.971 (3) | 98.680 (7) |
| unit cell volume [Å$^3$] | 1414.43 (14) | 3276.2 (6) |
| Number of molecules per unit cell | 1 | 2 |
| calculated density [g cm$^{-3}$] | 1.156 | 1.095 |
| radiation applied | $\mu$(Mo-K$\alpha$) $\lambda$ = 0.71073 | |
| Angular range 2$\vartheta$ [°] | 2.92-21.26 | 2.04-22.72 |
| Number of counted reflexes | 12035 | 14564 |
| Number of data/parameters | 3138/262 | 8074/586 |
| GOOF fit index | 1.062 | 1.064 |
| Divergence coefficients R for I>2σ(I) | R1 = 0.0671 wR2 = 0.1493 | R1 = 0.0595 wR2 = 0.1509 |
| Divergence coefficients R for all reflexes | R1 = 0.0926 wR2 = 0.1620 | R1 = 0.0762 wR2 = 0.1608 |

| | $[Et_2Zn_4(OEt)_2(Bq)_4]$ Example 7 | $\{[Zn(BTZ)_2](^tBuZnBTZ)_2\}$ Example 8 |
|---|---|---|
| molecular formula | $C_{60}H_{52}N_4O_6Zn_4$ | $C_{60}H_{50}N_4O_4S_4Zn_3$ |
| Mr | 1186.54 | 1215.39 |
| crystallographic system | Monoclinic | monoclinic |
| space group | P 2$_1$/c (no.14) | P 2$_1$ (no. 4) |
| temperature [K] | 100 (2) | 100 (2) |
| a [Å] | 12.7490 (7) | 11.4520 (5) |
| b [Å] | 11.1180 (6) | 14.4330 (9) |
| c [Å] | 23.9520 (12) | 18.2980 (10) |
| α [°] | 90.00 | 90.00 |
| β [°] | 102.192 (3) | 100.66 (3) |
| γ [°] | 90.00 | 90.00 |
| unit cell volume [Å3] | 3318.5 (3) | 2972.3 (3) |
| Number of molecules per unit cell | 2 | 2 |
| calculated density [g cm$^{-3}$] | 1.187 | 1.358 |
| radiation applied | $\mu$(Mo-K$\alpha$) $\lambda$ = 0.71073 | |
| Angular range 2$\vartheta$ [°] | 2.03-24.71 | 1.81-23.81 |
| Number of counted reflexes | 8150 | 8848 |
| Number of data / parameters | 4848/334 | 7848/677 |
| GOOF fit index | 1.113 | 1.080 |
| Divergence coefficients R for I>2σ(I) | R1 = 0.0520 wR2 = 0.1310 | R1 = 0.0782 wR2 = 0.1552 |
| Divergence coefficients R for all reflexes | R1 = 0.0662 wR2 = 0.1385 | R1 = 0.1022 wR2 = 0.1686 |

TABLE 2-continued

Crystallographic data of [($^t$Bu)$_2$Zn$_4$(μ$_4$-O)(Meq)$_4$], [($^i$Bu)$_2$Zn$_4$(μ$_4$-O)(Meq)$_4$], [Et$_2$Zn$_4$(OEt)$_2$(Bq)$_4$], {[Zn(BTZ)$_2$] ($^t$BuZnBTZ)$_2$} and Zn$_{10}$q$_{12}$(CO$_3$)$_4$

| | Zn$_{10}$q$_{12}$(CO$_3$)$_4$ Example 9, 10 and 11 |
|---|---|
| molecular formula | C$_{112}$H$_{72}$N$_{12}$O$_{24}$Zn$_{10}$ |
| M$_r$ | 2623.52 |
| crystallographic system | Trigonal |
| space group | R-3 (no. 148) |
| temperature [K] | 100 (2) |
| a [Å] | 22.3630 (19) |
| b [Å] | 22.3630 (19) |
| c [Å] | 54.763 (3) |
| α [°] | 90.00 |
| β [°] | 90.00 |
| γ [°] | 120 |
| unit cell volume [Å$_3$] | 23718 (3) |
| Number of molecules per unit cell | 6) |
| calculated density [g cm$^{-3}$] | 1.102 |
| radiation applied | μ(Mo-Kα) λ = 0.71073 |
| Angular range 2𝜗[°] | 2.14-23.23 |
| Number of counted reflexes | 7487 |
| Number of data/parameters | 6679/475 |
| GOOF fit index | 1.027 |
| Divergence coefficients R for I>2σ(I) | R1 = 0.0542 wR2 = 0.1398 |
| Divergence coefficients R for all reflexes | R1 = 0.0797 wR2 = 0.1535 |

The invention claimed is:

1. A compound having the general formula (R')$_x$Zn$_y$(L)$_z$(A)$_n$(XR)$_m$, wherein L is represented by the structure

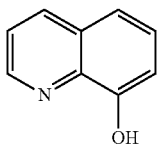

substituted optionally with alkyl groups;

A is an inorganic anion selected from O$^{2-}$ and CO$_3^{2-}$,
X is oxygen or sulfur,
R' is C1-C10 alkyl, straight or branched, benzyl, phenyl, cyclohexyl or halogen,
R is hydrogen, alkyl or aryl,
x is a number from 0 to 6,
y is a number from 1 to 12,
z is a number from 1 to 12,
n is a number from 1 to 6, and
m is 0.

2. The compound according to claim 1, wherein the inorganic anion A is O$^{2-}$.

3. The compound according to claim 1, wherein x is a number from 1 to 6.

4. A compound selected from the group consisting of:
(a) [(Znq$_2$)$_2$($^t$BuZnOH)$_2$];
(b) [(Znq$_2$)$_2$(EtZnOH)$_2$];
(c) [(tBu)$_2$Zn$_4$(μ4-O)(Meq)$_4$];
(d) [(iPr)$_2$Zn$_4$(μ4-O)(Meq)$_4$]; and
(g) Zn$_{10}$q$_{12}$(CO$_3$)$_4$; and
wherein:
q is 8-hydroxyquinoline;
Meq is 5,7-dimethyl-8-hydroxyquinoline;
Et is ethyl;
iPr is isopropyl; and
$^t$Bu is t-butyl.

5. The compound according to claim 1, wherein the inorganic anion A is CO$_3^{2-}$.

* * * * *